United States Patent

Zygmont et al.

[11] Patent Number: 6,080,126
[45] Date of Patent: Jun. 27, 2000

[54] COTTON SWABS WITH SOFT TIPS

[75] Inventors: Joseph Frank Zygmont, Killingworth; William Howard Schmitt, Branford, both of Conn.

[73] Assignee: Chesebrough-Pond's USA Co., divison of Conopco, Inc., Greenwich, Conn.

[21] Appl. No.: 09/134,219

[22] Filed: Aug. 14, 1998

[51] Int. Cl.[7] .................................................. A61M 35/00
[52] U.S. Cl. ................. 604/1; 600/569; 600/572
[58] Field of Search ...................... 604/1–3, 11; 600/569, 600/572

[56] References Cited

U.S. PATENT DOCUMENTS

| | | |
|---|---|---|
| 1,903,664 | 4/1933 | Yutts . |
| 2,153,144 | 4/1939 | Gilfillan . |
| 2,813,286 | 11/1957 | Strader . |
| 3,090,080 | 5/1963 | Pellicone et al. . |
| 3,255,494 | 6/1966 | Bloch et al. . |
| 3,452,650 | 7/1969 | Cobb . |
| 4,718,889 | 1/1988 | Blasius, Jr. et al. . |
| 4,820,259 | 4/1989 | Stevens ......................................... 604/1 |
| 5,127,899 | 7/1992 | Schmerse, Jr. . |
| 5,158,532 | 10/1992 | Peng et al. . |
| 5,531,671 | 7/1996 | Bennett . |
| 5,709,010 | 1/1998 | Bennett . |
| 5,766,143 | 6/1998 | Bennett . |

FOREIGN PATENT DOCUMENTS 990564  6/1976  Canada .

*Primary Examiner*—John G. Weiss
*Assistant Examiner*—Dennis Ruhl
*Attorney, Agent, or Firm*—Milton L. Honig

[57] ABSTRACT

A swab is described formed of a paper stick having opposite ends of less paper density than the rest of the stick. An absorbent covering such as cotton is placed around the ends. The stick is obtained by rolling a paper having left and right edges harmonically cut with at least two amplitude maxima and at least one amplitude minima. Softer stick ends are achieved through this structural arrangement. A cut paper used for forming the swab stick and a manufacturing process are also described.

22 Claims, 3 Drawing Sheets

COTTON SWABS WITH SOFT TIPS

BACKGROUND OF THE INVENTION

1. Field of the Invention

The invention relates to cotton swabs useful in cleaning the ear or applying cosmetics.

2. The Related Art

Swabs having an absorbent covering on the tip and an elongated stem are well known. Cotton is generally used as the absorbent tip covering material. Stem materials are often of wood, rolled paper or plastic. Conventional swabs are typically constructed by applying the absorbent covering directly to the ends of the stem. An adhesive may be used to more firmly hold the absorbent covering in place upon the swab.

Cost and performance problems have long been associated with traditional swabs. U.S. Pat. No. 5,127,899 (Schmerse, Jr.) raises the issue of eardrum damage when swabs are improperly applied to clean the outer ear. The patent suggests that injuries may be avoided by positioning a flat disc at each of the distal ends of the swab beneath the cotton coverings. This disc is sized to prevent entry of the swab into the human ear canal. Although a useful improvement, the flat disc increases the rigidity of the cotton covered tips rendering them harder. There are also manufacturing difficulties with providing a flat disc to the ends of the swab stem.

U.S. Pat. No. 4,718,889 (Blasius, Jr. et al.) discloses the use of a resilient cushion positioned between the end of the stem and the absorbent covering. This resilient cushion is intended to provide some degree of protection against damage in the event that the stem does protrude through the absorbent covering. However, the stem is not rendered substantially softer and is also more difficult to manufacture.

U.S. Pat. No. 5,531,671, U.S. Pat. No. 5,709,010 and U.S. Pat. No. 5,766,143 all to Bennett describe swabs having sticks which at each end are formed with a conical member flared outwardly and having a hollow center. The hollow flared conical members provide expanded swab ends rendering the tips softer and larger yet employing less cotton and paper in its manufacture. A die-cut paper is employed for forming the stick. Mirror image curved left and right edges border a length of the paper.

It is evident that further improvements are necessary in swab technology. These improvements should focus on softer ends and less construction materials to reduce costs.

Accordingly, it is an object of the present invention to provide a swab with softer ends than those currently available.

Another object of the present invention is to provide a swab requiring less construction material to reduce costs while still exhibiting improved functionality.

Still another object of the present invention is to provide a swab whose ends are uniformly without tabs or flags protruding from the swab stick.

SUMMARY OF THE INVENTION

A swab is provided that includes:

an elongate stem with first and second ends opposite one another, the stem being formed from a rolled paper with left and right edges harmonically cut with at least two amplitude maxima and at least one amplitude minima, the left and right edges when rolled forming the respective first and second ends; and an absorbent covering surrounding each of the first and second ends.

Any manner of harmonic cut may be suitable along left and right edges. Harmonic for purposes of this invention is defined as alternating protrusions and valleys along edges forming the stem ends. Illustrative harmonic cuts are rounded sinusoidal, serrated triangular, and square-toothed patterns. However, a serrated or square-toothed pattern with up to 90 degree angles at the valley or amplitude minima is less preferred than rounded or greater than 90 degree angled patterns. Sharp angled contact points along left and right edges result in weak areas where tear lines can form.

In a first embodiment, the harmonic cut is a sinusoidal curved pattern of left and right edges. One aspect of this embodiment is that leading and trailing edges should be cut orthogonal to a minima of the amplitudes, i.e. across the lowest or deepest portion of the harmonic curves. When the leading and trailing edges are cut across amplitude maxima of left and right edges, protruding tabs or flags at the ends of the stem result after windup of the paper into a stem (i.e. stick).

In a second embodiment, the harmonic cut is a toothed pattern with flat amplitude maxima and flat amplitude minima. Curved corners rather than right angled ones transition the minima into the maxima areas. Leading and trailing edges are serrated. The serrated edges of this embodiment orthogonally traverse amplitude maxima. Advantageously the intersection of leading and of trailing edges with the amplitude maxima occur across different regions of the amplitude maxima.

Serration of leading and trailing edges is preferred over a straight cut because the former glues more securely than the latter. However, along areas adjacent the left and right edges, serration results in an unwanted tab or flag. The problem is avoided by terminating the serration for a short distance with a straight cut near the respective left and right edges.

A further aspect of the invention is that of a process for manufacturing swabs. Steps of the process include:

(a) preparing a swab stick by cutting a paper to achieve left and right edges in harmonic pattern with at least two amplitude maxima and at least one amplitude minima along each edge;

(b) rolling the cut paper into a stick; and (c) placing an absorbent covering around each end of the swab stick.

DETAILED DESCRIPTION OF THE DRAWINGS

The above features, advantages and objectives of the present invention will be more fully appreciated through the following detailed discussion, references being made to the drawing in which.

DETAILED DESCRIPTION

Now it has been discovered that soft tipped swabs can be obtained from a rolled paper whose left and right edges follow a harmonic pattern with at least two amplitude maxima and at least one amplitude minima. The maxima and minima along left and right edges preferably are symmetrically aligned or nearly symmetrically aligned.

Figure 1:
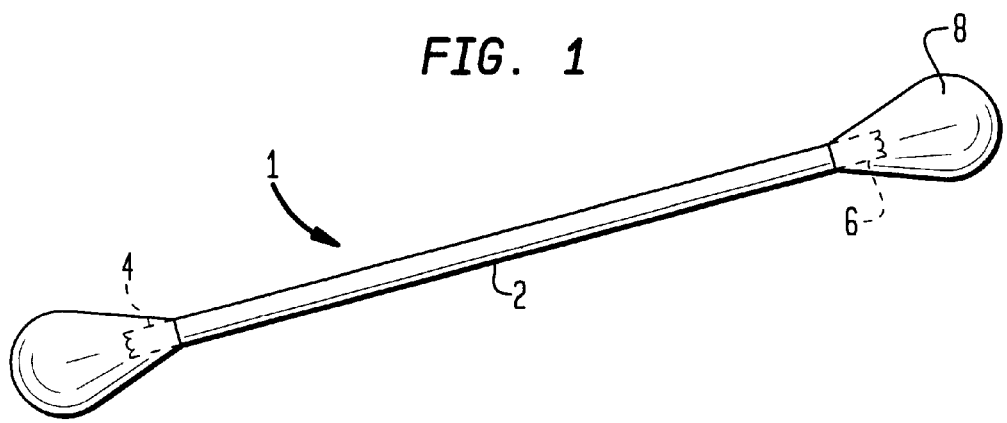
FIG. 1 is a plan perspective view of the swab according to the present invention.

FIG. 1 illustrates a swab 1 with an elongated stem 2 with first and second ends 4, 6 at opposite extremities from one another. An absorbent covering 8 surrounds ends 4, 6. Cotton is the most preferred absorbent covering. However, synthetic or other natural materials of flexible and absorbent properties can also be utilized. For example, the absorbent covering could be formed of rayon fibers, polyurethane or other foamed or fibered synthetic materials.

Figure 2:
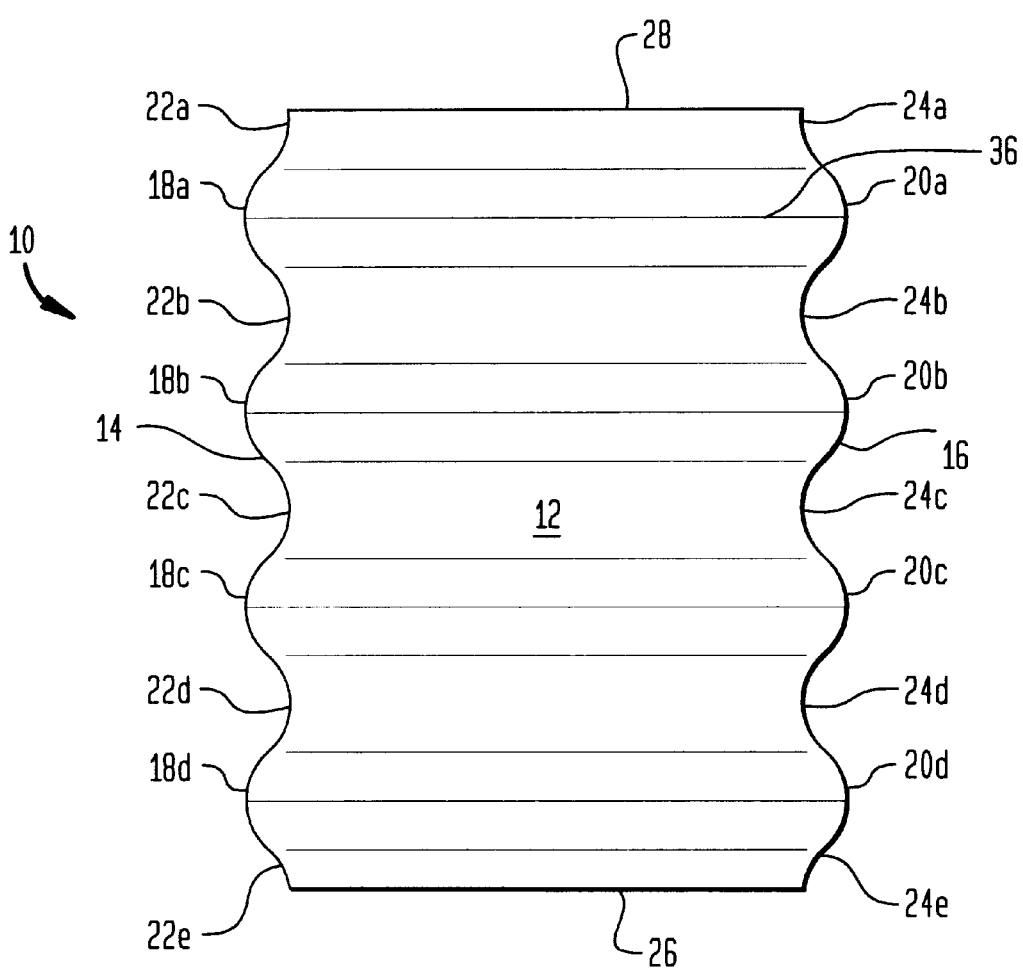
FIG. 2 is a top plan view of a first embodiment of a die-cut paper forming a stem for the swab described in FIG. 1.

FIG. 2 illustrates a first embodiment of a die-cut paper 10. The paper is fashioned from a flat cellulosic sheet 12 with mirror image curved left and right edges 14, 16 cut down a length thereof. These edges trace a sinusoidal pattern with four left amplitude maxima 18a, b, c, d and four right amplitude maxima 20a, b, c, d. The sinusoidal curve also includes five left amplitude minima 22a, b, c, d, e and five right amplitude minima 24a, b, c, d, e. At opposite ends of the paper are leading and trailing edges 26 and 28 straight cut and parallel to one another. Leading and trailing edges 26 and 28 orthogonally intersect respective amplitude minima 22e–24e and 22a–24a.

Figure 3:
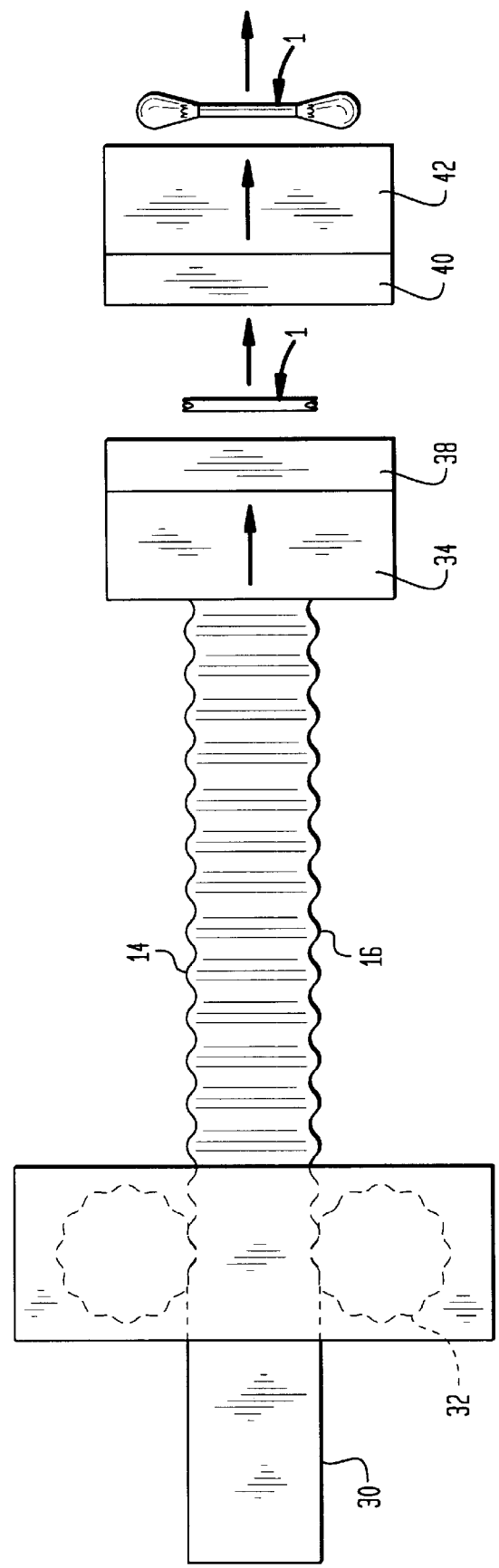
FIG. 3 is a highly schematic view of the process for preparing swab sticks of the present invention.

Stem and conical members are unitarily formed as a swab stick in a process outlined in FIG. 3. The process begins with preparation of the die-cut paper shown in FIG. 2. A sheet of continuous roll paper 30 is fed between a pair of cutters 32 having rotating knives. The cutters are in the form of a wheel (e.g. 3 inch diameter) set to deliver a certain number of amplitude maxima and minima per inch of paper. Change in the wheel size allows for alternating the amplitude. Each of the cutters and paper are synchronized to deliver exact mirror image left and right cut edges. Thereafter a crimping roller 34 places a multitude of creases 36, as shown in FIG. 2, parallel to one another along a length of the cut paper. The creases assist in rolling of the stick. In an alternate embodiment, the crimping roller 34 may be positioned prior to the cutters.

Downstream from crimping, the die-cut left and right edged paper passes across a second cutter 38 oriented perpendicular to movement of the die-cut sheet to sever sections from the sheet. Each severing cut is timed to occur along an amplitude minima resulting in leading edge 26 and trailing edge 28 shown in FIG. 2.

Subsequently each segment of die-cut, severed paper is tightly rolled at a rolling station 40. Adhesives may optionally be spread on the die-cut paper to assist in preventing unraveling of the stick. Cotton fibers are then applied at station 42 in the conventional well-known manner to each of the swab stick ends thereby forming the cotton absorptive covering. By way of reference to the rolling and cotton fiber application steps, these are known from U.S. Pat. No. 3,090,080 (Pellicone et al.), U.S. Pat. No. 3,452,650 (Cobb) and Canadian Patent 990,564 (Cottrell).

Figure 4:
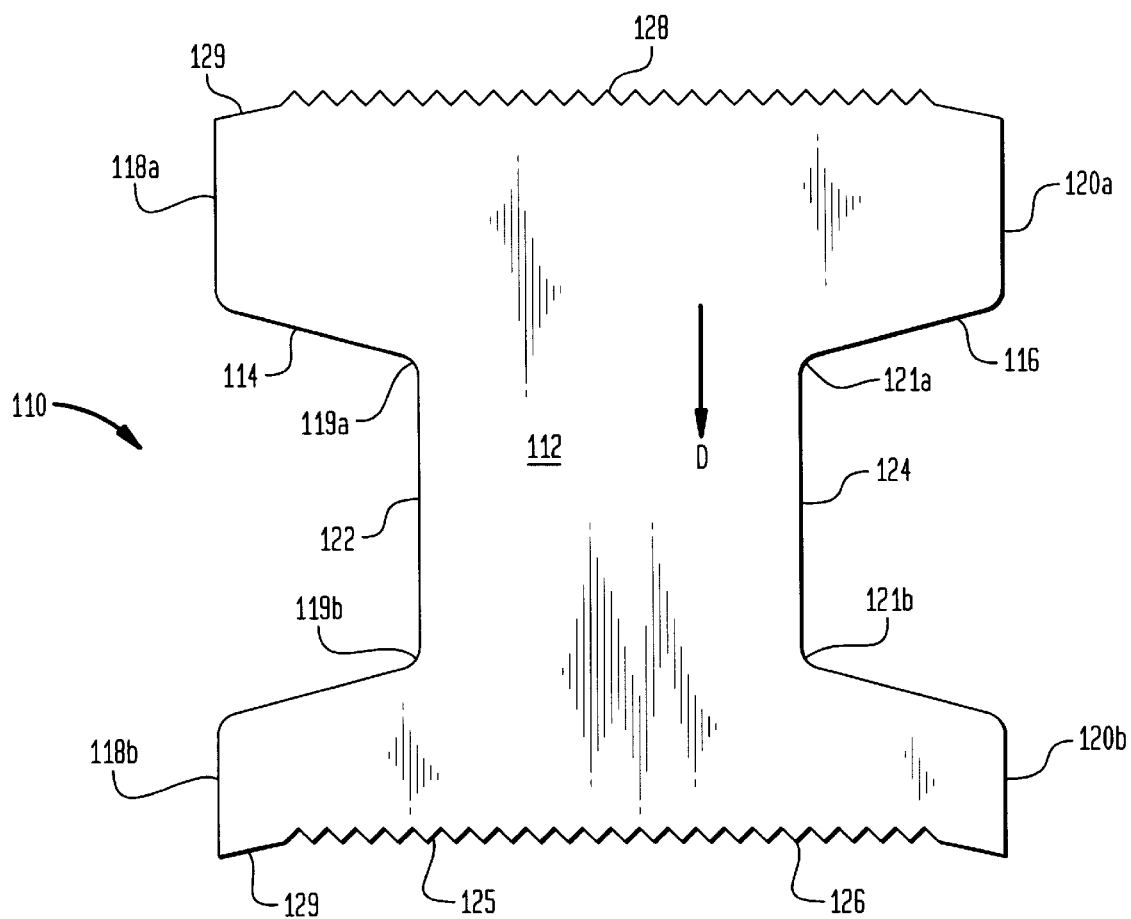
FIG. 4 is a top plan view of a second embodiment of a die-cut paper forming a stem for the swab described in FIG. 1.

FIG. 4 presents a second embodiment of a die-cut paper 110. The paper is fashioned from a flat cellulosic sheet 112 with mirror image saw-toothed left and right edges 114, 116 cut down a length thereof. These edges exhibit two left amplitude maxima 118a, b and two right amplitude maxima 120a, b. A single amplitude minima 122 and 124 is formed at respective left and right edges positioned between the respective amplitude maxima. Curved corners 119a, b and 121a, b transition the amplitude minima into the maxima regions of the cut. At opposite ends of the paper are leading and trailing edges 126 and 128 having a central serrated portion 125 and straight cut end portions 129. Leading and trailing edges 126 and 128 orthogonally intersect respective amplitude maxima 118b–120b and 118a–120a.

Figure 5:
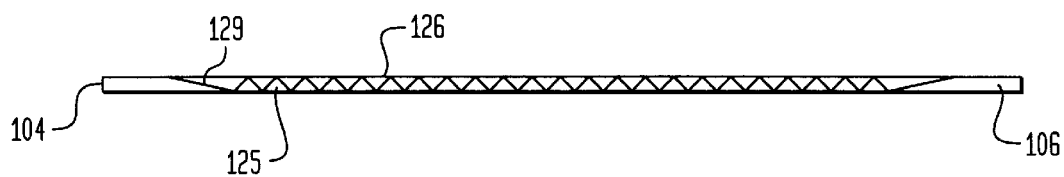
FIG. 5 is a side elevational view of the rolled stem formed from the die-cut paper of FIG. 4.

FIG. 5 illustrates the rolled die-cut paper 110. The resultant stick is achieved by tightly rolling in direction D the die-cut paper 110 beginning from leading edge 126 to trailing edge 128. Adhesive is placed along leading edge 126 to seal same preventing unraveling. First and second ends 4, 6 avoid any tabs or flags protruding by having a straight cut portion 129 on the adhesively glued trailing edge 128.

The foregoing description and drawing illustrate selected embodiments of the present invention and in light thereof various modifications will be suggested to one skilled in the art all of which are within the spirit and purview of this invention.

What is claimed is:

1. A swab comprising:
   an elongate stem with first and second ends opposite one another, the stem being formed from a rolled paper with left and right edges harmonically cut with each edge having at least two amplitude maxima and at least one amplitude minima, the left and right edges when rolled forming the respective first and second ends; and
   an absorbent covering surrounding each of the first and second ends.

2. A swab according to claim 1 wherein the absorbent covering is cotton.

3. The swab according to claim 1 wherein there are from 3 to 5 amplitude maxima on each of the left and right edges of the paper.

4. The swab according to claim 1 further comprising a leading and a trailing edge traversing respective amplitude minima.

5. The swab according to claim 1 further comprising a leading and a trailing edge traversing respective amplitude maxima.

6. The swab according to claim 1 wherein the amplitude maxima are two in number.

7. The swab according to claim 1 wherein the amplitude maxima are flat straight edges.

8. The swab according to claim 1 wherein the amplitude minima are flat straight edges.

9. The swab according to claim 5 wherein an area under a first of the amplitude maxima is larger than an area under a second of the amplitude maxima.

10. The swab according to claim 1 wherein there are no angles less than 120 degrees along either of said left or right edges with the exception of any intersection at leading and trailing edges.

11. The swab according to claim 5 wherein the leading edge is serrated along a central section and at either ends is a straight cut section.

12. A paper with left and right edges harmonically cut with each edge having at least two amplitude maxima and at least one amplitude minima, the left and right edges when rolled forming respective first and second ends of an elongate stem.

13. The paper according to claim 12 wherein there are from 3 to 5 amplitude maxima on each of the left and right edges of the paper.

14. The paper according to claim 12 further comprising a leading and a trailing edge traversing respective amplitude minima.

15. The paper according to claim 12 further comprising a leading and a trailing edge traversing respective amplitude maxima.

16. The paper according to claim 12 wherein the amplitude maxima are two in number.

17. The paper according to claim 12 wherein the amplitude maxima are flat straight edges.

18. The paper according to claim 12 wherein the amplitude minima are flat straight edges.

19. The paper according to claim 12 wherein an area under a first of the amplitude maxima is larger than an area under a second of the amplitude maxima.

20. The paper according to claim 12 wherein there are no angles less than 120 degrees along either of said left or right edges with the exception of any intersection at leading and trailing edges.

21. The paper according to claim 12 further comprising a leading and a trailing edge wherein the leading edge is serrated along a central section and at either ends has a straight cut section.

22. A process for preparing a swab comprising:

(i) preparing a swab stick by cutting a paper along left and right edges in harmonic pattern defining along each edge at least two amplitude maxima and at least one amplitude minima;

(ii) rolling the cut paper into a stick; and (iii) placing an absorbent covering around opposite ends of the rolled stick.

\* \* \* \* \*